United States Patent [19]

Suzuki et al.

[11] 4,323,486

[45] Apr. 6, 1982

[54] ALBUMIN-FIXED RESIN, PRODUCTION THEREOF, AND THERAPEUTICAL USE THEREOF

[75] Inventors: Hideaki Suzuki; Gentaro Yamashita, both of Koganei, Japan

[73] Assignee: Teijin Limited, Osako, Japan

[21] Appl. No.: 205,997

[22] Filed: Nov. 12, 1980

[30] Foreign Application Priority Data

Nov. 12, 1979 [JP] Japan .................................. 54-145503

[51] Int. Cl.$^3$ ........................... C07G 7/00; C08H 1/00; C08L 89/00; C09J 3/24
[52] U.S. Cl. ................................ 525/54.1; 260/112 B; 260/121; 260/122; 210/767; 527/204; 527/207
[58] Field of Search .................. 260/6, 18 PN, 112 B, 260/121, 122

[56] References Cited

U.S. PATENT DOCUMENTS

| | | | |
|---|---|---|---|
| 2,289,775 | 7/1942 | Graves ..................................... | 260/6 |
| 2,460,980 | 2/1949 | Fraenkel-Conrat et al. ........ | 260/121 |
| 2,597,228 | 5/1952 | Cornwell et al. .................... | 260/121 |
| 2,852,477 | 9/1958 | Greenlee ......................... | 260/18 PN |
| 2,882,250 | 4/1959 | Baker ...................................... | 260/6 |
| 3,788,948 | 1/1974 | Kagedal et al. ................. | 260/112 B |
| 3,970,597 | 7/1976 | Sokolovsky et al. ................... | 260/6 |
| 4,119,589 | 10/1978 | Horn et al. ............................... | 260/6 |
| 4,182,695 | 1/1980 | Horn et al. ............................... | 260/6 |

OTHER PUBLICATIONS

Archives of Biochemistry and Biophysics, vol. 65, 1956, pp. 132-155, Tiselius, A. et al, "Protein Chromatography on Calcium Phosphate Columns".
Journal of Biological Chemistry, vol. 179, 1949, pp. 1063-1074, Schwimmer, S. et al, "Isolation and Properties of Crystalline α-Amylase from Germinated Barley".
Immunology, vol. 20, 1971, pp. 1061-1065, Sanderson, C. J. et al, "A Simple Method for Coupling Proteins to Insoluble Polysaccharides".

*Primary Examiner*—John Kight, III
*Assistant Examiner*—Nathan M. Nutter
*Attorney, Agent, or Firm*—Sherman & Shalloway

[57] ABSTRACT

The present invention provides an albumin-fixed resin comprising a crosslinked water-insoluble resin and albumin chemically bound thereto, said water-insoluble resin being a crosslinked epoxy resin containing about 1 to about 30 milliequivalents of amino groups and about 1 to about 50 milliequivalents of hydroxyl groups per gram thereof, said albumin being ionically bound to the amino groups of the epoxy resin and to the hydroxyl groups by hydrogen bonding, and the amount of said albumin fixed being at least about 25% by weight based on the epoxy resin, and also provides a process for producing the albumin-fixed resin, which comprises (1) (a) subjecting a polyepoxy compound containing at least two epoxy groups in the molecule and a polyamine compound containing at least two primary and/or secondary amino groups in the molecule to addition reaction in an inert medium to produce a fully crosslinked resin, or (b) subjecting said compounds to addition reaction to produce an insufficiently crosslinked pre-polymer, and then reacting the pre-polymer with at least one compound selected from the group consisting of organic polyisocyanates, organic polyisothiocyanates and organic polycarboxylic acid halides to crosslink it fully, and (2) contacting the resulting crosslinked epoxy resin containing about 1 to about 30 milliequivalents of amino groups and about 1 to about 50 milliequivalents of hydroxyl groups per gram thereof intimately with an aqueous solution containing albumin optionally after partially neutralizing the amino groups of the epoxy resin.

The albumin-fixed resin is useful for removing albumin-binding noxious substances such as bilirubin contained in the blood of a warm-blooded animal.

17 Claims, No Drawings

ALBUMIN-FIXED RESIN, PRODUCTION THEREOF, AND THERAPEUTICAL USE THEREOF

This invention relates to a water-insoluble polymer having a large quantity of albumin bound thereto, a process for its production, and its use for the removal of noxious substances in plasma.

Substances which adsorb proteins such as albumin have been known, and include, for example, such inorganic substances as activated carbon, porous glass, alumina, silica gel, bentonite and hydroxyappatite [see, for example, A. Tiselius, Arch. Biochem. & Biophys., Vol. 65, page 132 (1956)], and such organic substances as starch and gluten [see, for example, S. Schwimmer, J. Biolog. Chem. 179, 1063 (1949)]. These substances, however, have the defect that they merely permit physical adsorption of proteins, and cannot lead to firm fixing of large quantities of these proteins thereto partly because these proteins generally have a molecular weight of more than ten thousand.

Substances capable of permitting chemical binding of albumin thereto are also known. For example, cyanogen bromide-activated agarose is known as a substance capable of fixing albumin thereto by a covalent bond, and a basic ion exchange resin, as a substance capable of fixing albumin thereto by an ionic bond. Furthermore, as a special substance, an albumin-fixed polysaccharide having albumin fixed thereto by a covalent bond is known. This substance is produced by oxidizing a polysaccharide such as cellulose or agarose with periodic acid, reacting it with the amino groups of albumin, and reducing the reaction product with sodium borohydride [see, for example, C. J. Sanderson et al., Immunology, Vol. 20, page 1061 (1971)]. These substances, however, have the defect that the number of sites to which albumin can be bonded is not sufficiently large, and their ability to fix a large quantity of albumin thereto firmly is low, and the method of producing such an albumin-bound substance is generally complex. A substance which has the ability to bind the largest amount of albumin thereto can permit fixation of about 200 mg at most per gram of it in the dried state.

It is an object of this invention to provide a cross-linked water-insoluble polymer having large amounts of amino groups and large amounts of hydroxyl groups, which can fix a large quantity of albumin firmly thereto.

Another object of this invention is to provide a novel albumin-fixed resin comprising a crosslinked epoxy resin having large amounts of amino groups and hydroxy groups and a large quantity of albumin firmly bound by ionic bonding to the amino groups of the resin and by hydrogen bonding to its hydroxyl groups.

Still another object of this invention is to provide a process for producing the novel albumin-fixed resin.

A further object of this invention is to provide a method for removing an albumin-binding noxious substance contained in the blood of a warm-blooded animal using the aforesaid novel albumin-fixed resin.

Other objects of this invention will become apparent from the following description.

According to one aspect of this invention, these objects and advantages of this invention are achieved by an albumin-fixed resin comprising a crosslinked water-insoluble resin and albumin chemically bound thereto, said water-insoluble resin being a crosslinked epoxy resin containing about 1 to about 30 milliequivalents of amino groups and about 1 to about 50 milliequivalents of hydroxyl groups per gram of the resin, said albumin being bound ionically to the amino groups of the epoxy resin and by hydrogen bonding to its hydroxyl groups and being fixed in an amount of not more than about 25% by weight based on the epoxy resin.

Investigations of the present inventors have shown that a substance having only those sites which permit bonding of albumin by an ionic bond (e.g., the amino group) or a substance having only those sites which permit bonding of albumin by hydrogen bonding (e.g., the hydroxyl group) cannot achieve effective fixation of albumin, and that only a substance which have these two types of sites together in proximity can have albumin effectively fixed thereto.

These investigations also led to the discovery that such a substance can be conveniently given by a crosslinked epoxy resin obtained by the addition reaction of a polyepoxy compound and a polyamine compound. The crosslinked epoxy resin has the advantage that large amounts of amino groups and hydroxyl groups can be incorporated, and therefore, it can fix a large amount of albumin firmly thereto.

The crosslinked epoxy resin used in this invention is water-insoluble and has about 1 to about 30 milliequivalents, preferably about 2 to about 20 milliequivalents, especially preferably about 4 to about 10 milliequivalents, of amino groups per gram of the resin and about 1 to about 50 milliequivalents, preferably about 2 to about 35 milliequivalents, especially preferably about 4 to about 25 milliequivalents, of hydroxyl groups per gram of the resin.

The albumin in this invention may be any albumin derived from various animals including man.

In the albumin-fixed resin of this invention, albumin is fixed to the amino groups, usually secondary or tertiary amino groups, of the epoxy resin through an ionic bond and to the hydroxyl groups through hydrogen bonding.

The albumin-fixed resin of this invention contains albumin in the fixed state in an amount of at least about 25% by weight, preferably about 25 to about 150% by weight, especially preferably about 50 to about 150% by weight, based on the weight of the epoxy resin.

The albumin-fixed resin of this invention can be produced by contacting the crosslinked epoxy resin intimately with an aqueous solution containing albumin. The contacting is usually carried out preferably at about 5° C. to about 30° C. Through this contacting, chemical bonds, i.e. an ionic bond and hydrogen bond, form between the crosslinked epoxy resin and albumin. It is believed that by the amino groups of the crosslinked epoxy resin, albumin is positioned at a specified site of the epoxy resin, and bonded through a hydrogen bond by the hydroxyl groups of the epoxy resin whereby albumin is firmly fixed to the epoxy resin.

The ionic bond and hydrogen bond form very rapidly, but the formation of these bonds is affected by the form of the crosslinked epoxy resin, the efficiency of contacting, etc. Thus, in the case of dipping the crosslinked epoxy resin in an aqueous solution containing albumin, the contacting is carried out usually for about 1 to 60 minutes.

During the contacting, the concentration of the aqueous albumin solution is preferably about 0.5 to about 5% by weight.

Before contact with the aqueous albumin solution, the crosslinked epoxy resin may be contacted with an acid to neutralize the amino groups at least partly. For this purpose, a phosphate buffer having a pH of about 7, for example, may be used preferably. When the neutralized crosslinked epoxy resin is contacted with the aqueous solution of albumin, fluctuations in the pH of the aqueous solution after contacting are reduced.

Contacting between the crosslinked epoxy resin and the aqueous albumin solution can be effected conveniently by, for example, dipping the epoxy resin in the aqueous solution, or passing the aqueous solution through a column packed with the epoxy resin. As a special method, this can also be performed by passing the aqueous solution through a tube or a slender tube having a dimension corresponding to a hollow filament, at least the surface of which is made of the crosslinked epoxy resin by such means as coating. As described hereinbelow, the crosslinked epoxy resin used in this invention can be easily produced as fine particles, and therefore, the aforesaid contacting operation can be advantageously performed by the aforesaid dipping method or column method using such fine particles of the resin. The fine particles of the crosslinked epoxy resin have an average diameter of usually about 0.1 to about 2 mm, preferably about 0.5 to about 1.5 mm.

The albumin-fixed resin of this invention can be favorably used for removing an albumin-binding noxious substance contained in the blood.

According to this invention, the crosslinked epoxy resin used in this invention can be produced by (a) subjecting a polyepoxy compound having at least two epoxy groups in the molecule and a polyamide compound having at least two primary and/or secondary amino groups in the molecule to addition reaction in an inert medium to form a fully crosslinked resin, or (b) subjecting these compounds to addition reaction in an inert medium to form an insufficiently crosslinked pre-polymer, and reacting the resulting pre-polymer with at least one compound selected from the group consisting of organic polyisocyanates, organic polyisothiocyanates and organic polycarboxylic acid halides, to crosslink it fully.

Compounds having two or three epoxy groups in the molecule, such as di- or tri-glycidyl ethers, are preferably used as the polyepoxy compound having at least two epoxy groups in the molecule. Polyglycidyl ethers having up to 6 epoxy groups in the molecules, such as sorbitol polyglycidyl ether, can also be used.

Especially preferred diglycidyl ethers include a compound of the following formula

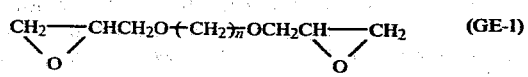

wherein n is a number of 2 to 10, a compound of the following formula

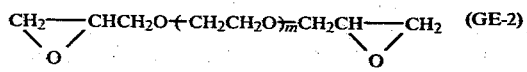

wherein m is a number of 2 to 10, glycerol diglycidyl ether, bisphenol A diglycidyl ether, hydroquinone diglycidyl ether, resorcinol diglycidyl ether and mixtures of these compounds.

Specific examples of the compounds of formula (GE-1) are ethylene glycol, diglycidyl ether, trimethylene glycol diglycidyl ether, tetramethylene glycol diglycidyl ether, hexamethylene diglycidyl ether, and decamethylene diglycidyl ether.

Examples of the compound of formula (GE-2) are diethylene glycol diglycidyl ether and other polyethylene glycol diglycidyl ethers in which m is up to 10.

Examples of the triglycidyl ethers are glycerol triglycidyl ether, 1,1,1-trimethylolpropane triglycidyl ether, phloroglucinol triglycidyl ether, triglycidyl isocyanurate and mixtures of these compounds.

The polyamine compound used in this invention is a compound containing at least two primary and/or secondary amino groups in the molecule, and optionally having a tertiary amino group in addition to the above amino groups.

Examples of preferred polyamine compounds are aliphatic, alicyclic and aromatic diamines having no tertiary amino group in the molecule, and polyalkylenepolyamines of the following formula

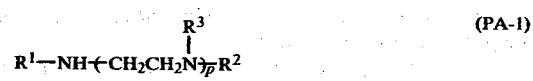

wherein $R^1$ and $R^2$ are identical or different and each represents a hydrogen atom or an alkyl, alkenyl, hydroxyalkyl, aryl or aralkyl group, $R^3$ represents a hydrogen atom or a beta-aminoethyl group, p is a number of 2 to 10, provided that two or more $R^3$ groups, independently from each other, may be hydrogen atoms or beta-aminoethyl groups, which may have a tertiary amino group.

Examples of preferred aliphatic diamines are compounds of the following formula

wherein q is an integer of 2 to 10, such as ethylenediamine, trimethylenediamine, tetramethylenediamine, hexamethylenediamine and decamethylenediamine, and diamines of the formula

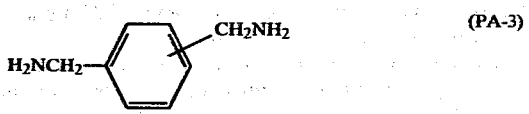

such as p-xylylenediamine and m-xylylenediamine.

Examples of preferred alicyclic diamines are piperazine, 2,5-dimethylpiperazine and diaminocyclohexanes of the following formula

such as 1,4-diaminocyclohexane and 1,3-diaminocyclohexane.

Examples of preferred aromatic diamines are diaminobenzenes of the following formula

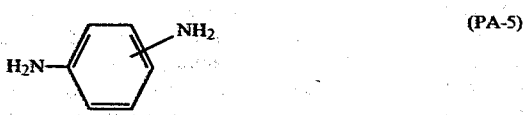

such as 1,4-diaminobenzene and 1,3-diaminobenzene and diaminobisphenylene compounds of the following formula

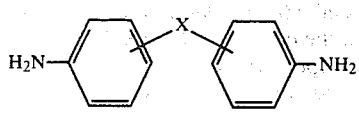   (PA-6)

wherein X represents a bond, a methylene group, a dimethylmethylene group, or an oxygen atom, such as 4,4'-diaminodiphenylene, 3,4'-diaminodiphenylene, 3,3'-diaminodiphenylene, 2,4'-diaminodiphenylene, 4,4'-diaminodiphenylmethane, 2,2-bis(p-aminophenyl)propane and 4,4'-diaminodiphenylether.

As regards $R^1$ and $R^2$ in formula (PA-1) representing the polyalkylenepolyamine, the alkyl group is preferably an alkyl group having 1 to 3 carbon atoms such as methyl, ethyl and propyl; the alkenyl group is preferably an alkenyl group having 2 or 3 carbon atoms, such as vinyl, propenyl or isopropenyl; the hydroxyalkyl group is preferably a hydroxyalkyl group having 1 to 3 carbon atoms, such as hydroxymethyl, hydroxyethyl or hydroxypropyl; the aryl group is preferably phenyl, tolyl or naphthyl; and the aralkyl group is preferably benzyl or beta-phenethyl.

Examples of the polyalkylene polyamine in which $R^1$ and $R^2$ are hydrogen atoms are compounds of the following formulae

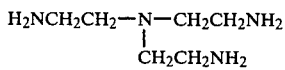
(one $R^3$ is beta-aminoethyl, and the other $R^3$ groups are hydrogen atoms, p = 2)

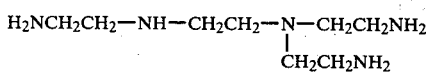
(two $R^3$ groups are hydrogen atoms, one $R^3$ is beta-aminoethyl, p = 3)

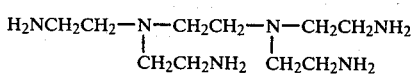
(one $R^3$ is hydrogen atom, two $R^3$ groups are beta-aminoethyl groups, p = 3)

From these exemplified compounds, those skilled in the art will be able to understand easily specific examples of compounds of formula (PA-1) in which $R^1$ and $R^2$ are other than hydrogen atoms.

The polyepoxy compound and the polyamine compound are reacted in an inert medium, if desired in the presence of a surface-active agent, to give a fully crosslinked water-soluble epoxy resin.

According to another embodiment of this invention, the polyepoxy compound and polyamine compound are reacted in an inert medium, if desired in the presence of a surface-active agent, to give an insufficiently crosslinked pre-polymer, and the pre-polymer is then reacted with at least one compound selected from the group consisting of organic polyisocyanates, organic polyisothiocyanates and organic polycarboxylic acid halides to give a fully crosslinked water-insoluble epoxy resin.

In the reaction of the polyepoxy compound and polyamine compound, the epoxy groups of the polyepoxy compound add to the primary and/or secondary amino groups of the polyamine compound as schematically shown below.

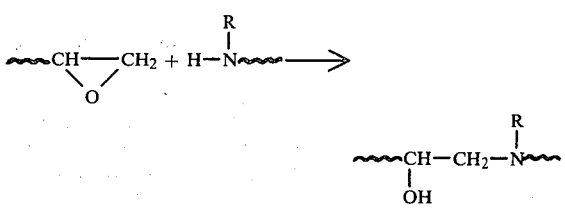

In order to produce a fully crosslinked epoxy resin by the reaction of the polyamine compound and the polyepoxy compound, it is necessary to adjust properly the proportions of these compounds, i.e. the equivalents of the epoxy groups and the amino groups, the reaction time, etc. It has been observed that even when either one of the starting materials is used in excess in a proportion stoichiometrically permitting full crosslinking, it is most important to perform the reaction at a temperature exceeding about 30° C.

Thus, according to the first embodiment (a), the reaction of the polyepoxy compound with the polyamine compound is carried out at a temperature of generally about 20° C. to about 100° C., preferably about 30° to about 70° C. In the second embodiment (b), the reaction is carried out at a temperature of generally about −30° C. to about 40° C., preferably about 20° to about 30° C.

The proportions of the starting materials in the first embodiment are such that the amount of the epoxy groups of the epoxy compound is 0.8 to 2.0 equivalents, especially preferably 1.05 to 1.5 equivalents, per equivalent of the primary and/or secondary amino groups of the polyamine compound.

The same proportions of the starting materials may be used in the second embodiment. But preferably, the proportions of the starting materials in the second embodiment is such that the amount of the epoxy groups of the epoxy compound is generally 0.5 to 2.0 equivalents, especially 0.8 to 1.5 equivalents, per equivalent of the primary and/or secondary amino groups of the polyamino compound.

The reaction of the polyepoxy compound with the polyamine compound is carried out in an inert medium. When required (for example, when water is used as the medium but the two starting materials do not have sufficient solubility in water and it is desirable to increase their solubility), a water-soluble organic medium such as tetrahydrofuran and dioxane may be added to the reaction system in order to perform the reaction smoothly. The reaction of the polyepoxy compound and the polyamine compound may be performed in solution, suspension or emulsion.

In the first embodiment, the reaction of the polyepoxy compound with the polyamine compound may preferably be carried out in the following manner.

Predetermined amounts of the polyepoxy compound and the polyamine compound are dissolved in a water-insoluble or sparingly water-soluble inert organic medium, and reacted at a temperature of preferably not more than about 30° C. until the reaction mixture substantially remains a uniform solution. Then, the solution is suspended in water, and reacted further preferably at a temperature of at least about 30° C. to produce a water-insoluble, fully crosslinked, spherical epoxy resin.

Examples of preferred water-insoluble or sparingly water-soluble inert organic media include aromatic hydrocarbons such as benzene, toluene and xylene, halogenated hydrocarbons such as chlorobenzene, methylene chloride, chloroform, dichloroethane, trichloroethane and trichloroethylene, aliphatic hydrocarbons such as hexane, heptane, octane and cyclohexane, and mixtures of these.

To perform the suspending operation stably, there is preferably used a suspension stabilizer such as bentonite, polyacrylic acid, pectin, polyvinyl alcohol, gelatin, talc, barium sulfate and calcium carbonate. In order to perform the suspending operation smoothly, the specific gravity of the dispersion medium is desirably increased by dissolving a water-soluble inorganic salt such as sodium chloride, sodium phosphate or sodium sulfate in water.

In another manner, predetermined amounts of the polyepoxy compound and the polyamine compound are dissolved in an aqueous medium, and reacted at a temperature of preferably not more than about 30° C. until the reaction mixture substantially remains a uniform solution. Then, the solution is suspended in a water-insoluble or sparingly water-soluble inert organic medium, and further reacted at a temperature of preferably at least about 30° C. to produce a water-insoluble, spherical, fully crosslinked epoxy resin.

Examples of the water-insoluble or sparingly water-soluble inert organic media may be the same as those given hereinabove.

To perform the suspending operation stably, there is preferably used a dispersing agent, for example a lower alkyl cellulose such as methyl cellulose, ethyl cellulose or butyl cellulose. Preferably an organic monocarboxylic acid having at least 5 carbon atoms is preferably used as a dispersing aid. Examples of the organic monocarboxylic acid are aliphatic monocarboxylic acids such as caproic acid, caprylic acid, myristic acid, palmitic acid, stearic acid and oleic acid, and aromatic monocarboxylic acids such as benzoic acid and toluic acid.

When the dispersing aid is used, there are obtained spherical particles of a crosslinked epoxy resin on the surface of which large quantities of the secondary and/or tertiary amino groups are distributed. It is believed that the dispersing aid forms a salt with the amino groups used in of the polyamine compound used, and at this time the hydrophobic portion of the dispersing aid is directed toward the inert organic medium as a dispersing medium, thereby giving spherical particles having a large quantity of the amino groups distributed on their surface.

Treatment of the resulting spherical particles with an aqueous solution of an alkali such as sodium hydroxide leads to a product having free amino groups by releasing the organic carboxylic acid.

In any of the aforesaid preferred modes in the first embodiment, it is generally desirable to use the polyepoxy compound in an amount exceeding the equivalent of the polyamine compound. These compounds are used in a total amount of about 2 to about 80% by weight, preferably about 5 to about 60% by weight, especially preferably about 10 to about 50% by weight, in the solution.

The substantially uniform solution obtained by reacting this solution can be suspended in the dispersing medium in a solution-to-medium volume ratio of from 1:2 to 1:100, preferably from 1:2.5 to 1:50, especially preferably from 1:3 to 1:10.

The spherical particles of the crosslinked epoxy resin obtained have sizes varying depending upon the ratio of the solution to the dispersion medium. Generally, the sizes of the spherical particles can be controlled by adjusting the speed of stirring. The particle diameter of the crosslinked epoxy resin is preferably about 0.1 to about 2 mm, especially preferably about 0.5 to about 1.5 mm.

In the second embodiment described above, the reaction of producing the insufficiently crosslinked prepolymer from the polyepoxy compound and the polyamine compound is carried out in the same reaction medium as described above at a temperature of preferably below about 30° C. The resulting pre-polymer is then reacted with at least one compound selected from organic polyisocyanates, organic polyisothiocyanates and organic polycarboxylic acid halides.

Organic diisocyanates are preferred as the organic polyisocyanate. Examples are hexamethylene diisocyanate, lysine diisocyanate, hydrogenated diphenylmethane diisocyanate, isophorone diisocyanate, hydrogenated tolylene diisocyanate, tolylene diisocyanate, diphenylmethane diisocyanate, naphthylene diisocyanate, xylylene diisocyanate, and tolidine diisocyanate.

Organic diisothiocyanates are preferred as the organic polyisothiocyanate. Examples include hexamethylene diisothiocyanate, tolylene diisothiocyanate and diphenylmethane diisothiocyanate.

Preferred acid halides of the organic polycarboxylic acid are chlorides or bromides, especially chlorides, of organic di- or tri-carboxylic acids, especially organic dicarboxylic acids. Examples of the organic di- or tricarboxylic acids include aliphatic dicarboxylic acids such as oxalic acid, malonic acid, succinic acid, glutaric acid, adipic acid, azelaic acid, sebacic acid and brassylic acid, aromatic dicarboxylic acids such as phthalic acid, isophthalic acid and terephthalic acid, and aromatic tricarboxylic acids such as trimellitic acid and trimesic acid. Chlorides of these organic carboxylic acids are used preferably.

In the reaction with the pre-polymer, such a polyvalent compound acts as a crosslinking agent for the prepolymer to give a crosslinked epoxy resin.

The term "insufficiently crosslinked", as used in the present application means that the resulting product still has crosslinkable reactive functional groups, i.e. amino and epoxy groups, and the reaction can still be effected between these reactive functional groups, or the product no longer has a reactive functional group but cannot be used as a water-insoluble polymer. Accordingly, the insufficiently crosslinked pre-polymer includes not only a substantially linear polymer having a relatively low molecular weight, but also a polymer which is crosslinked but not to such an extent as to become substantially water-insoluble.

The reaction of the pre-polymer can be performed, for example, by molding the pre-polymer into such a shape as a film or fibers and then treating the molded article with the crosslinking agent or a solution of it in an aprotic inert organic solvent; or by adding the crosslinking agent to a solution of the prepared pre-polymer in water or an inert organic solvent.

In the latter case, when the solution of the prepolymer is an aqueous solution, it is possible to dissolve the crosslinking agent in an aprotic inert organic medium such as methylene chloride, chloroform, cyclohexane, toluene or xylene, and add the solution to the solution of the pre-polymer to perform the reaction. According to this method, the crosslinked epoxy resin can be obtained as spherical particles.

In the latter case, when the solution of the prepolymer is a solution of an inert organic solvent, it is possible to add the crosslinking agent directly to the solution of the pre-polymer or add it after dissolving it in an aprotic inert organic solvent.

The reaction of the pre-polymer with the crosslinking agent is carried out at about −30° C. to about 100° C., preferably about 20° to about 30° C. The reaction time is about 5 minutes to about 300 minutes. When the crosslinking agent is used as a solution in an aprotic inert organic solvent, the concentration of the crosslinking agent is preferably 0.05 to 5% by weight.

The crosslinked epoxy resin so obtained is then after-treated as required, and then contacted with a solution of albumin in the manner described hereinabove to give the albumin-fixed resin in accordance with this invention.

For example, the resin obtained as a result of solidification of the reaction mixture is pulverized to a suitable size, washed (usually with water), dried and as required, sieved. The crosslinked epoxy resin formed as particles in the reaction system is separated by filtration, centrifugal separation, etc., washed, dried, and as required, sieved.

The albumin-fixed resin provided by the process of this invention is conveniently used to remove albumin-binding noxious substances present in blood. For example, it combines with such an albumin-binding substance as thyroxine, triiodothyronine, bilirubin, uric acid, bile acid, guanidine, various indoles, acetylcholine, barbituric acid, digitoxin and salicyclic acid. It is known that these noxious substances are difficult to remove effectively by adsorption on activated carbon, dialysis, etc.

Accordingly, in another aspect, the present invention provides a method for removing noxious substances capable of being bonded to albumin from a solution containing said noxious substances, which comprises contacting the albumin-fixed resin of this invention intimately with a solution containing albumin-binding noxious substances contained in the blood of a warm-blooded animal.

The solution containing albumin-binding noxious substances may, for example, be blood, plasma separated from the blood, a dilution of the blood or plasma with a blood isotonic solution such as physiological saline.

Accordingly, the present invention also provides a method for removing an albumin-binding noxious substance from the blood of a warm-blooded animal, which comprises extracorporeally drawing the blood of a warm-blooded animal from which it is desired to remove an albumin-binding noxious substance contained therein, contacting the albumin-fixed resin of this invention intimately with the blood, the plasma separated therefrom, or a dilution of the blood or plasma with a blood isotonic solution, and thereafter returning the blood, plasma or the dilution thereof from which the albumin-binding noxious substances have been removed to the body of the animal.

The method of this invention is especially advantageously applied to the removal of bilirubin from the blood of a patient with hepatic failure, etc. In hepatic failure, toxins increase in the blood of the patient and in a serious case, induce hepatic coma. The cause of hepatic coma has not been completely elucidated, but is believed to be due partly to the presence of bilirubin in the blood.

Since the albumin-fixed resin of this invention has a large quantity of albumin, a component of blood, bonded thereto, it has excellent compatibility with the blood and is well antithrombotic. Because of these properties, the albumin-fixed resin of this invention is also useful as a fabricated article for artificial organs such as artificial kidneys, an antithrombotic coating material for catheters, etc.

As stated hereinabove, when the crosslinked epoxy resin provided by this invention is contacted with a solution containing albumin such as blood or plasma, the albumin-fixed resin of this invention results. Accordingly, it is readily appreciated that when the crosslinked epoxy resin is contacted with blood, etc. containing an albumin-binding noxious substance, the albumin-fixed resin of this invention forms and acts to remove the noxious substance. This embodiment is preferred and included within the scope of this invention.

The following Examples illustrate the present invention more specifically.

All percentages in these Examples are by weight.

The concentration of albumin in its aqueous solution is determined from the absorbance of the aqueous solution at 280 nm in its ultraviolet absorption spectrum.

Throughout the present application, the equivalents of amino groups and hydroxyl groups are measured in the following manner.

About 1 g of a dried fine powder having a size of about 0.01 to about 0.1 mm as a sample is precisely weighed, and put into about 100 ml of distilled water. Then, 0.05 N hydrochloric acid is added dropwise at room temperature with stirring using phenolphthalein as an indicator. The equivalent of amino groups in the sample is determined from the amount of the hydrochloric acid consumed.

About 1 g of a dried fine powder having a size of about 0.01 to about 0.1 mm is precisely weighed and dispersed in 100 ml of dehydrated toluene. About 3.0 g of precisely weighed acetic anhydride is added, and the mixture is reacted at 40° C. for 1 hour with stirring. The reaction mixture is cooled, and the polymer is separated by filtration. The polymer is washed with 50 ml of dehydrated toluene, and the filtrate and the washing are combined. The mixture is then titrated with 0.05 N alcoholic sodium hydroxide solution to a neutralization point. The total equivalent of amino groups and hydroxyl groups in the fine powder is calculated from the amount titrated with the alcoholic sodium hydroxide solution, and the equivalent of the hydroxyl groups is obtained by subtracting the equivalent of the amino groups from the total equivalent.

The concentration of bilirubin in plasma is determined by the Evelyn-Malloy method [see J. Biol. Chem. 119, 480 (1937)].

EXAMPLE 1

(1) A 300 ml. three-necked separable flask equipped with a stirrer and a thermometer was charged with 5.2 g (0.05 mole) of diethylenetriamine and 50 ml of distilled water, and while the contents of the flask were stirred at 25° C., 25 ml of a tetrahydrofuran solution containing 12.1 g (0.06 mole) of 1,4-butanediol diglycidyl ether was gradually added dropwise. The mixture was stirred at this temperature for 1 hour, and when the viscosity of the mixture rose, the stirrer was detached from the flask. When the reaction mixture was allowed to stand for 2 hours, it completely solidified to a gel. The gel was pulverized, well washed with water and then dried to afford 17.0 g of a polymer.

The resulting dried polymer contained about 90% by weight of particles having a particle diameter of about 0.5 to about 1.0 mm and had an average particle diameter of about 0.7 mm. The polymer contained about 8.0 milliequivalents of amino groups and about 6.5 milliequivalents of hydroxyl groups per gram thereof.

(2) A portion (2.0 g) of the polymer obtained in (1) above was taken into a 300 ml flask equipped with a stirrer, and 300 ml of a 1.0% aqueous solution of bovine serum albumin was added. The mixture was stirred for 1 hour, and filtered to afford a polymer having albumin bound thereto. The albumin content of the filtrate was measured, and the amount of albumin reacted with the polymer was calculated. It was found that 0.32 g of albumin was bonded per gram of the base polymer.

EXAMPLE 2

The procedure of Example 1, (1) was repeated except that 3.48 g (0.03 mole) of hexamethylenediamine and 2.06 g (0.02 mole) of diethylenetriamine were used instead of 5.2 g of diethylenetriamine. There was obtained 17.5 g of a water-insoluble polymer. The polymer was pulverized and dried. The polymer had an average particle diameter of 0.7 mm, and contained about 6.5 milliequivalents of amino groups and about 6.5 milliequivalents of hydroxyl groups per gram thereof.

The polymer particles were reacted with albumin in the same way as in Example 1, (2). It was found that 0.35 g of albumin was bonded per gram of the polymer.

EXAMPLE 3

(1) In the same way as in Example 2, 3.48 g (0.03 mole) of hexamethylenediamine and 2.06 g (0.02 mole) of diethylenetriamine were reacted with 1,4-butanediol diglycidyl ether. There was obtained 17.2 g of a water-insoluble polymer. The polymer was then pulverized and dried to afford polymer particles having an average particle diameter of about 0.7 mm.

A portion (3.0 g) of the polymer was added to 150 ml of a 0.6% toluene solution of 4,4'-diphenylmethane diisocyanate, and the mixture was stirred at 25° C. for 1 hour. After the reaction, the resulting polymer was separated by filtration, well washed with methanol, and dried to afford 3.8 g of the polymer.

The resulting dried polymer particles had an average particle diameter of about 0.7 mm, and contained about 6.2 milliequivalents of amino groups and about 6.4 milliequivalents of hydroxyl groups per gram thereof.

(2) A portion (1.2 g) of the polymer obtained in (1) above was packed into a column having a diameter of 15 mm and a length of 60 mm, and 0.1% aqueous solution (1.5 liters) of bovine serum albumin was passed through the column at a flow rate of 1 ml/min. The concentration of albumin in the effluent from the column was measured periodically. The concentration of albumin was zero until the amount of the effluent reached 0.5 liter. Thereafter, the concentration of albumin in the effluent gradually increased, and 1.5 liters of the effluent was required until the concentration of albumin in it reached 0.1%. The amount of albumin bonded to the polymer was found to be 0.83 g per gram of the polymer.

EXAMPLE 4

(1) A 500 ml three-necked flask equipped with a stirrer and a thermometer was charged with 1.6 g (0.014 mole) of hexamethylenediamine, 0.48 g (0.0047 mole) of diethylenetriamine and 20 ml of distilled water, and with stirring at 25° C., 4.68 g (0.024 mole) of glycerol diglycidyl ether was gradually added. The mixture was stirred at this temperature for 30 minutes, and then 300 ml of a 0.6% toluene solution of 4,4'-diphenylmethane diisocyanate and 20 mg of polyoxyethylene sorbitan monopalmitate as a surfactant were added. The mixture was vigorously stirred for 1 hour at 25° C. After the reaction, the resulting particulate polymer was separated by filtration, washed well with methanol, and dried to afford 8.5 g of a water-insoluble polymer.

The resulting polymer had an average particle diameter of about 0.5 mm, and contained about 5.8 milliequivalents of amino groups and about 0.5 milliequivalent of hydroxyl groups per gram of thereof.

(2) A portion (1.0 g) of the polymer obtained in (1) above was dipped in a phosphate buffer having a pH of 7.4 to neutralize the amino groups in it, and packed into a column having a diameter of 15 mm and a length of 60 mm. Then, 1.8 liters of a 0.1% aqueous solution of human serum was passed through the column at a flow rate of 1 ml/min. The concentration of albumin in the effluent from the column was periodically measured. The concentration of albumin was zero until the amount of the effluent reached 1 liter. When 1.6 liters of the effluent was collected, the concentration of albumin was 0.01%. Until the concentration of albumin in the effluent reached 0.1%, 1.8 liters of the effluent was required. Based on this result, the amount of albumin bonded to the polymer was calculated. It was found that 1.6 g of albumin was bonded per gram of the polymer.

EXAMPLE 5

The procedure of Example 4, (1) was repeated except that 2,4-tolylene diisocyanate was used instead of 4,4'-diphenylmethane diisocyanate. There was obtained 8.3 g of particles of a water-insoluble polymer.

The polymer particles had an average particle diameter of about 0.5 mm and contained about 5.5 milliequivalents of amino groups and about 9.0 milliequivalents of hydroxyl groups per gram of the polymer.

A portion (1.0 g) of the polymer was dipped in a phosphate buffer having a pH of 7.4 to neutralize the amino groups in it. Then, the polymer was collected by filtration, and dipped in 200 ml of a 1.0% aqueous solution of bovine serum albumin, and stirred at 25° C. for 1 hour. The polymer was separated by filtration, and the amount of albumin remaining in the aqueous solution was measured. It was found that 1.24 g of albumin was bonded per gram of the polymer.

EXAMPLE 6

The procedure of Example 4, (1) was repeated except that hexamethylene isothiocyanate was used instead of 4,4'-diphenylmethane diisocyanate. There was obtained 8.5 g of a water-insoluble polymer.

The resulting polymer had an average particle diameter of about 0.5 mm, and contained about 5.6 milliequivalents of amino groups and about 9.1 milliequivalents of hydroxyl groups per gram of the polymer.

A portion (1.0 g) of the polymer was treated with a phosphate buffer in the same way as in Example 5, and then reacted with an aqueous solution of bovine serum albumin in the same way as in Example 5 to afford a polymer having 0.95 g of albumin bonded per gram of the polymer.

EXAMPLE 7

(1) A 500 ml three-necked flask equipped with a stirrer and a thermometer was charged with 1.6 g (0.015 mole) of hexamethylenediamine, 0.69 g (0.0047 mole) of triethylenetetramine and 20 ml of distilled water. With stirring at 25° C., 4.68 g (0.024 mole) of glycerol diglycidyl ether was gradually added. The mixture was stirred for 30 minutes at this temperature. Then, 300 ml of a 0.6% toluene solution of isophthaloyl dichloride and 20 mg of polyoxyethylene sorbitan monopalmitate as a surfactant were added, and the mixture was vigorously stirred for 3 hours at 25° C. After the reaction, the resulting particulate polymer was collected by filtration, dipped in a 0.1 N aqueous solution of sodium hydroxide, washed successively with methanol and distilled water, and then dried to afford 6.9 g of a water-insoluble polymer as particles.

The polymer particles obtained had an average particle diameter of 0.5 mm, and contained about 6.2 milliequivalents of amino groups and about 9.8 milliequivalents of hydroxyl groups per gram thereof.

(2) A portion (1.0 g) of the resulting polymer was treated with a phosphate buffer in the same way as in Example 5, and then reacted with an aqueous solution of bovine serum albumin. There was obtained a polymer having 0.82 g of albumin bonded per gram thereof.

EXAMPLE 8

The procedure of Example 7 was repeated except that 0.48 g (0.0047 mole) of diethylenetriamine was used instead of 0.69 g of triethylenetetramine, and terephthaloyl dichloride was used instead of the isophthaloyl dichloride. There was obtained 6.1 g of a water-insoluble polymer as particles.

The polymer particles had an average particle diameter of 0.5 mm, and contained 5.8 milliequivalents of amino groups and 9.6 milliequivalents of hydroxyl groups per gram thereof.

A portion (1.0 g) of the polymer was treated with a phosphate buffer in the same way as in Example 5, and then reacted with an aqueous solution of a bovine serum albumin to afford a polymer having 0.80 g of albumin bonded thereto per gram of the polymer.

EXAMPLE 9

(1) A 500 ml three-necked flask equipped with a stirrer and a thermometer was charged with 7.3 g (0.05 mole) of triethylenetetramine, 2.47 g (0.0076 mole) of triglycidyl isocyanurate and 40 ml of distilled water, and they were stirred at 50° C. for 3 hours to afford a uniform solution. Then, 1.2 g (0.0083 mole) of sorbitol polyglycidyl ether was added to the reaction mixture and reeacted at 50° C. for 2 hours. Then, the reaction mixture was cooled to 25° C., and 400 ml of a 0.6% toluene solution of 4,4'-diphenylmethane diisocyanate and 30 mg of polyoxyethylene sorbitol monopalmitate as a surfactant were added. The mixture was vigorously stirred for 1 hour. After the reaction, the resulting polymer as particles was separated by filtration, washed with methanol, and dried to afford 12.3 g of a water-insoluble polymer.

The polymer particles had an average particle diameter of 0.5 mm, and contained 5.5 milliequivalents of amino groups and 2.0 milliequivalents of hydroxyl groups per gram thereof.

(2) A portion (1.0 g) of the polymer was treated with a phosphate buffer in the same way as in Example 5, and then reacted with an aqueous solution of bovine serum albumin to afford a polymer having 0.76 g of albumin bonded thereto per gram of the polymer.

EXAMPLE 10

(1) A 300 ml three-necked separable flask equipped with a stirrer and a thermometer was charged with 3.2 g (0.028 mole) of hexamethylenediamine, 0.96 g (0.0094 mole) of diethylenetriamine and 40 ml of distilled water, and with stirring at 25° C., 9.36 g (0.046 mole) of glycerol diglycidyl ether was gradually added. The mixture was stirred for 20 minutes at this temperature, and then 300 ml of a 0.6% toluene solution of 4,4'-diphenylmethane diisocyanate and 20 mg of polyoxyethylene sorbitan monopalmitate as a surfactant were added. The mixture was stirred for 1 hour at 25° C. After the reaction, the polymer particles were separated by filtration, well washed with methanol, and dried to afford 13.0 g of a water-insoluble polymer as particles.

The polymer particles had an average particle diameter of 0.5 mm, and contained 12.0 milliequivalents of amino groups and 19.5 milliequivalents of hydroxyl groups per gram thereof.

(2) A portion (1.0 g) of the polymer was dipped in a phosphate buffer having a pH of 7.4, filtered, washed, and then dipped in 100 ml of an aqueous solution of plasma albumin in a concentration of 1.0 g/dl. The solution was slowly stirred to bond albumin to the polymer. It was found that 1 g of albumin was bonded per gram of the polymer.

(3) The albumin-bonded polymer was packed into a column having a diameter of 15 mm and a length of 60 mm, and 100 ml of plasma containing bilirubin in a concentration of 11.5 mg/dl was passed circulatingly through the column at a flow rate of 2 ml/min. for 6 hours. The total concentration of bilirubin in the plasma decreased to 4.5 mg/dl.

EXAMPLE 11

The polymer particles (1.0 g) produced by the method of Example 10, (1) was dipped in a phosphate buffer having a pH of 7.4, and packed into a column. Then, 100 ml of plasma containing bilirubin in a total concentration of 11.5 mg/dl was passed through the column circulatingly for 6 hours at a rate of 2 ml/min. After circulation, the concentration of bilirubin in the plasma decreased to 6.5 mg/dl.

EXAMPLE 12

(1) A 300 ml three-necked separable flask equipped with a stirrer and a thermometer was charged with 2.9 g (0.025 mole) of hexamethylenediamine, 1.9 g (0.005 mole) of bisphenol A diglycidyl ether and 4.04 g (0.02 mole) of glycerol diglycidyl ether. They were reacted in a solvent composed of 8 ml of chloroform and 4 ml of cyclohexane at 30° C. for 6 hours with stirring. Then, 1.0 g of triglycidyl isocyanurate was added, and 100 ml of water containing 10 g of sodium chloride and 0.5 g of bentonite as a dispersant was added to suspend and disperse the polymer solution. The reaction temperature was raised to 40° C., and the reaction was performed at this temperature for 1 hour with stirring to afford 8.5 g of a water-insoluble polymer in spherical particles.

The polymer particles obtained after washing and drying had an average particle diameter of 0.7 mm, and contained 5.5 milliequivalents of amino groups and 7.5 milliequivalents of hydroxyl groups per gram thereof.

1.0 g of the polymer was dipped in a phosphate buffer having a pH of 7.4, and then packed into a column. Then, 100 ml of plasma containing bilirubin in a total concentration of 10.8 mg/dl was circulatingly passed through the column at a rate of 2 ml/min. for 8 hours. The total concentration of bilirubin in the plasma decreased to 6.7 mg/dl.

EXAMPLE 13

A three-necked flask 300 ml equipped with a stirrer and a thermometer was charged with 3.2 g (0.028 mole) of hexamethylenediamine, 0.96 g (0.0094 mole) of diethylenetriamine and 40 ml of water, and 9.36 g (0.046 mole) of glycerol diglycidyl ether was added with stirring. The mixture was stirred at this temperature for 20 minutes. When the viscosity of the mixture rose, 2.0 g of benzoic acid and 160 ml of toluene containing 0.1 g of ethyl cellulose as a dispersant were added. The mixture was stirred to suspend and disperse the polymer solution. Then, the temperature of the polymer solution was raised to 40° C., and the reaction was performed for 1 hour to afford 13.0 g of spherical particles of water-insoluble polymer.

The insoluble polymer particles had an average particle diameter of 0.7 mm, and contained 12.3 milliequivalents of amino groups and 20.0 milliequivalents of hydroxyl groups per gram thereof.

A portion (1.0 g) of the polymer was dipped in a phosphate buffer having a pH of 7.4, and then packed into a column. Then, 100 ml of plasma containing bilirubin in a total concentration of 10.2 mg/dl was passed circulatingly through the column at a rate of 2 ml/min. for 4 hours. The concentration of total concentration of bilirubin in the plasma was decreased to 4.7 mg/dl.

What we claim is:

1. An albumin-fixed resin comprising a crosslinked water-insoluble resin and albumin chemically bound thereto, said water-insoluble resin being a crosslinked epoxy resin containing about 1 to about 30 milliequivalents of at least one of primary, secondary, and tertiary amino groups and about 1 to about 50 milliequivalents of hydroxyl groups per gram thereof, said albumin being ionically bound to the amino groups of the epoxy resin and to the hydroxyl groups by hydrogen bonding, and the amount of said albumin fixed being at least about 25% by weight based on the epoxy resin.

2. The albumin-fixed resin of claim 1 wherein said crosslinked epoxy resin contains about 2 to about 20 milliequivalents of amino groups and about 2 to about 35 milliequivalents of hydroxyl groups per gram thereof.

3. The albumin-fixed resin of claim 2 wherein the crosslinked epoxy resin contains about 4 to about 10 milliequivalents of amino groups and about 4 to about 25 milliequivalents of hydroxyl groups per gram thereof.

4. The albumin-fixed resin of claim 1 wherein the amount of albumin fixed is about 25 to about 150% by weight based on the epoxy resin.

5. The albumin-fixed resin of claim 1 wherein the crosslinked epoxy resin is derived from a polyepoxy compound and a polyamine compound.

6. The albumin-fixed resin of claim 1 wherein the crosslinked epoxy resin is derived from an insufficiently crosslinked pre-polymer obtained by reacting a polyepoxy compound with a polyamine compound, and at least one compound selected from the group consisting of organic polyisocyanates, organic polyisothiocyanates and organic polycarboxylic acid halides.

7. A process for producing the albumin-fixed resin of claim 1, which comprises (1) (a) subjecting a polyepoxy compound containing at least two epoxy groups in the molecule and a polyamine compound containing at least two primary and/or secondary amino groups in the molecule to addition reaction in an inert medium to produce a fully crosslinked resin, or (b) subjecting said compounds to addition reaction to produce an insufficiently crosslinked pre-polymer, and then reacting the pre-polymer with at least one compound selected from the group consisting of organic polyisocyanates, organic polyisothiocyanates and organic polycarboxylic acid halides to crosslink it fully, and (2) contacting the resulting crosslinked epoxy resin containing about 1 to about 30 milliequivalents of amino groups and about 1 to about 50 milliequivalents of hydroxyl groups per gram thereof intimately with an aqueous solution containing albumin optionally after partially neutralizing the amino groups of the epoxy resin.

8. The process of claim 7 wherein the polyepoxy compound is a di- or tri-glycidyl ether.

9. The process of claim 8 wherein the diglycidyl ether is selected from a compound of the formula

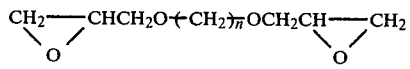

wherein n is a number of 2 to 10, a compound of the formula

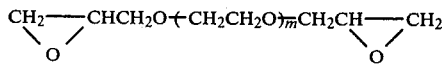

wherein m is a number of 2 to 10, glycerol diglycidyl ether, bisphenol A diglycidyl ether, hydroquinone diglycidyl ether, resorcinol diglycidyl ether and mixtures thereof.

10. The process of claim 8 wherein the triglycidyl ether is selected from the group consisting of glycerol triglycidyl ether, 1,1,1-trimethylolpropane triglycidyl ether, phloroglucinol triglycidyl ether, triglycidyl isocyanurate and mixtures thereof.

11. The process of claim 7 wherein the polyamine compound is an aliphatic diamine, an alicyclic diamine, an aromatic diamine, or a polyalkylenepolyamine of the formula

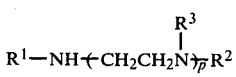

wherein $R^1$ and $R^2$ are identical or different, and each represents a hydrogen atom, or an alkyl, alkenyl, hydroxyalkyl, aryl or aralkyl group, $R^3$ represents a hydrogen atom or a beta-aminoethyl group, and p is a number of 2 to 10, provided that two or more $R^3$ groups, independently from each other, may be hydrogen atoms or beta-aminoethyl groups.

12. The process of claim 11 wherein the aliphatic diamine is a compound of the following formula

wherein q is an integer of 2 to 10, or a compound of the formula

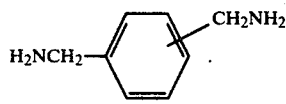

13. The process of claim 11 wherein the alicyclic diamine is piperazine, 2,5-dimethylpiperazine or diaminocyclohexane of the following formula

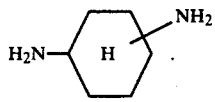

14. The process of claim 11 wherein the aromatic diamine is a diaminobenzene of the formula

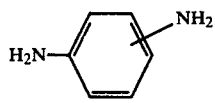

or a diaminobisphenylene compound of the formula

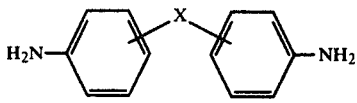

wherein X represents a bond, a methylene group, a dimethylmethylene group, or an oxygen atom.

15. The process of claim 7 wherein step (1), (a) is performed using 0.5 to 2.0 equivalents of the epoxy groups of the polyepoxy compound per equivalent of the primary and/or secondary amino groups of the polyamine compound.

16. The process of claim 7 wherein step (1), (b) is carried out using 0.5 to 2.0 equivalents of the epoxy groups of the polyepoxy compound per equivalent of the primary and/or secondary amino groups of the polyamine compound.

17. The process of claim 7 wherein the addition reaction of the polyepoxy compound and the polyamine compound is carried out by dispersing in an aqueous medium in the optional presence of a dispersant a solution of the polyepoxy compound and the polyamine compound in a water-insoluble or sparingly water-soluble inert organic solvent.

* * * * *